United States Patent [19]

Suyama

[11] Patent Number: 5,299,934
[45] Date of Patent: Apr. 5, 1994

[54] TEETH STRAIGHTENING BRACKET

[76] Inventor: Hajime Suyama, 6-1, Wachigawara, 2-Chone Miyazaki 880, Miyazaki-Shi, Japan

[21] Appl. No.: 852,244
[22] PCT Filed: Dec. 4, 1990
[86] PCT No.: PCT/JP90/01575
  § 371 Date: Jul. 16, 1992
  § 102(e) Date: Jul. 16, 1992
[87] PCT Pub. No.: WO91/07925
  PCT Pub. Date: Jun. 13, 1991

[30] Foreign Application Priority Data
  Dec. 5, 1989 [JP] Japan ................. 1-316796

[51] Int. Cl.[5] .............................................. A61C 3/00
[52] U.S. Cl. ................................................ 433/8; 433/10
[58] Field of Search ................................. 433/8, 9, 10

[56] References Cited

U.S. PATENT DOCUMENTS

| | | | |
|---|---|---|---|
| 3,496,637 | 2/1970 | Etengoff . | |
| 3,922,787 | 12/1975 | Fisher et al. | 433/8 |
| 4,242,085 | 12/1980 | Wallshein | 433/14 |
| 4,299,569 | 11/1981 | Frantz | 433/8 |
| 4,322,206 | 3/1982 | Reynolds | 433/9 |
| 4,419,078 | 12/1983 | Pletcher | 433/10 |
| 4,552,590 | 6/1985 | Pletcher | 433/15 |
| 4,799,882 | 1/1989 | Kesling | 433/8 |
| 4,842,512 | 6/1989 | Kesling | 433/8 |
| 4,917,602 | 4/1990 | Broussard | 433/8 |
| 5,044,945 | 9/1991 | Peterson | 433/8 |
| 5,062,794 | 11/1991 | Miura | 433/10 |
| 5,127,828 | 7/1992 | Suyama | 433/8 |
| 5,154,607 | 10/1992 | Hanson | 433/8 |
| 5,160,261 | 11/1992 | Peterson . | |
| 5,161,969 | 11/1992 | Pospisil et al. | 433/8 |

FOREIGN PATENT DOCUMENTS

| | | | |
|---|---|---|---|
| 0290247 | 11/1988 | European Pat. Off. | 433/10 |
| 45-37639 | 11/1970 | Japan . | |
| 64-25847 | 1/1989 | Japan . | |

Primary Examiner—Gene Mancene
Assistant Examiner—Cindy A. Cherichetti
Attorney, Agent, or Firm—Sheridan Ross & McIntosh

[57] ABSTRACT

A teeth straightening bracket comprises a base plate, a wire support disposed on the base plate, and a wire passage groove formed in the wire support for causing a correcting wire to pass therethrough under sliding movement. At least one of pair of engaging fingers for a binding wire is disposed on both sides of the wire support excepting for both longitudinal ends thereof. Further engaging fingers are preferably disposed on both longitudinal ends of the wire support in perpendicular to the longitudinal direction.

22 Claims, 12 Drawing Sheets

TEETH STRAIGHTENING BRACKET

DESCRIPTION

1. Technical Field

The present invention concerns a bracket used for correcting set of teeth.

2. Background Art

Heretofore, the bracket of this type, as shown in FIG. 14, comprises a base plate 14 and two wire supports 15, 15 disposed along both ends of the base plate 14, in which square sectioned wire passage grooves 16, 16 are formed in the center of the wire supports 15, 15, respectively.

For correcting irregular set of teeth (state of set of teeth in an irregular arrangement), for instance, by using the bracket C, the following method is usually adopted. That is, as shown in FIG. 16, after the first premolar 17 is extracted, the bracket C is bonded and fixed to the surface of each of teeth at first (refer to FIG. 15). Then, a round wire 6 of a circular cross section is extended under tension along the wire passage grooves 16, 16 of the individual bracket C (refer to FIGS. 14, 15), to correct the arrangement of the teeth along the backward and forward directions, as well as improve the twisting of the teeth and, while on the other hand, the gap after extracting the tooth is closed by moving a canine 19 toward a first molar by the resiliency of a rubber band (not illustrated).

In this case, the canine 19 is moved by the sliding movement, on the round wire 6 of the wire passage grooves 16, 16 of the bracket C bonded and fixed to the canine 10. However, in a case of using the bracket C, since the wire passage grooves 16, 16 are in a line-to-line contact with the round wire 6, a frictional force between them is large and, as a result, it takes a considerably long period of time for the correction.

In view of the above, with an aim of shortening the correction period, the present applicant has previously filed "Teeth Straightening Bracket" in Japanese Patent Application Hei 1-18345. The invention of the above-mentioned application provides, as shown in FIG. 11, a teeth straightening bracket comprising a base plate 11, two wire supports 12, 12 disposed along both ends of the base plate 11 and wire passage grooves 13, 13 formed respectively to the wire supports 12, 12, in which both side walls 13a, 13b of each of the wire passage grooves 13 are formed each in a semi-cylindrical shape and protruding to each other, as well as the bottom surface 13c of the passage groove 13 is formed as a semi-cylindrical convex shape extending from one side wall 13a to the other side wall 13b. In the bracket B of such a constitution, the wire passage grooves 13, 13 are in point-to-point contact with the round wire 6 and, as a result, since the frictional force can be reduced as compared with the line-to-line contact in the conventional bracket C, the period required for the correction can be shortened.

By the way, when the round wire 6 is extended under tension along with the wire passage grooves 13, 13 of the individual brackets B, it is necessary that the round wire 6 is not detached out of the wire passage grooves 13, 13. For this purpose, a hooked engaging finger 21 is disposed at both upper ends of the wire support 12 (FIG. 11), and a binding wire 8 is wound around the bracket B (also in the bracket C) so as to press it against the round wire 6, and the binding wire 8 is prevented from slipping off by the engaging finger 21 (refer to FIGS. 12, 13).

However, if the binding wire 8 is wound around the bracket B so as to press it against the round wire 6, the binding wire 8 presses the round wire 6 downward in FIG. 3. Therefore, when the canine 19 is moved toward the first molar 20 by the sliding movement of the wire passage groove 13 of the bracket B bonded and fixed to the canine 19 along the round wire 6 (refer to FIG. 16), the wire passage holes 13, 13 can not be smoothly moved under sliding along the round wire 6. As a result, an aimed object of shortening the period for the correction by reducing the frictional force exerting between the wire passage holes 13, 13 and the round wire 6 is hindered and can not be attained.

DISCLOSURE OF INVENTION

The present invention has an aim for dissolving the foregoing problems in the prior art and it provides, as a means therefor, a teeth straightening bracket comprising a base plate, wire supports disposed on the base plate, and a wire passage groove formed in the wire support, in which engaging fingers for a binding wire are disposed on both sides of the wire support.

Further, in a teeth straightening bracket in another embodiment of the present invention, comprising a base plate, a wire support disposed on the base plate and a wire passage group formed in the wire support for allowing a correcting wire to pass under sliding movement, engaging fingers for a binding wire are disposed on both sides of the wire support, such that the engaging fingers are disposed excepting for both ends thereof on at least one side and another engaging fingers are disposed to both longitudinal ends of the wire-support respectively.

In the teeth straightening bracket according to the present invention, a bonding wire can be wound around the teeth straightening bracket without pressing the bonding wire directly to the round wire upon preventing the round wire from slipping-off by the binding wire, while the teeth straightening bracket bonded and fixed to individual teeth can smoothly move slidingly on the round wire upon moving a tooth along a set of teeth and, as a result, a frictional force exerted between the wire passage groove and the round wire can be reduced to shorten the period for the correction. Further, in a case where another engaging fingers are disposed on both longitudinal ends of the wire support, the round wire is pressed by the binding wire thereby enabling to correct the set of teeth in the forward and backward directions and correct the twisting of a tooth.

BEST MODE FOR CARRYING OUT THE INVENTION

The present invention will hereinafter be described by way of its preferred embodiments with reference to the drawings.

Figure 1:
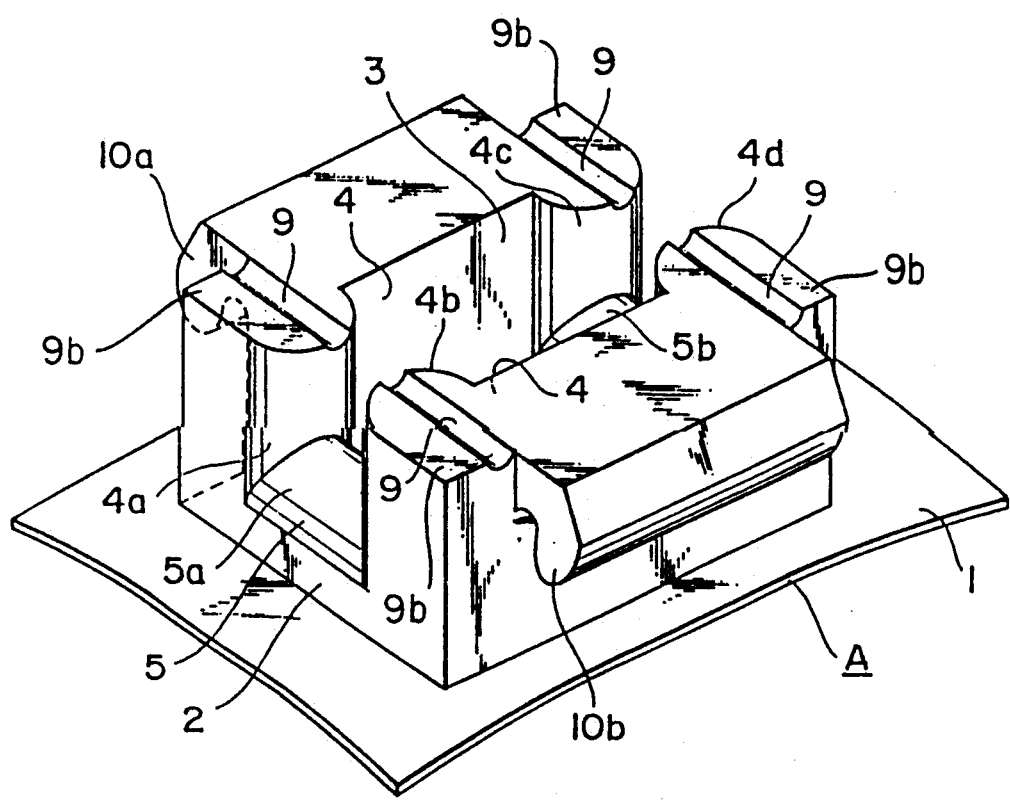
FIG. 1 is a perspective view showing a teeth straightening bracket according to the present invention.

FIG. 1 is a perspective view showing a teeth straightening bracket according to the present invention.

As shown in FIG. 1, a teeth straightening bracket A comprises a base plate 1 for bonding and fixing to the surface of a tooth, and a wire support 2 disposed to the upper surface of the base plate 1 and formed with a wire passage groove 3 along the longitudinal direction thereof (direction of the set of teeth).

Figure 4:
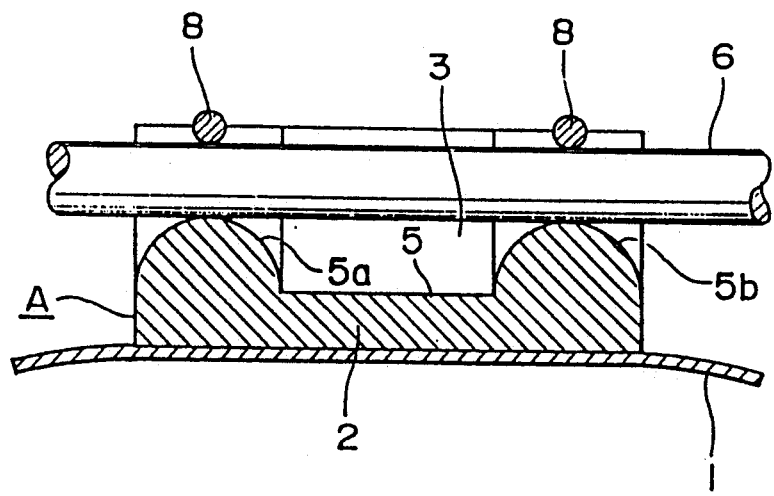
FIG. 4 is a cross sectional view taken along lines II—II in FIG. 2.

The base plate 1 is entirely curved so that it can fit against the surface of the tooth. In the wire passage groove 3 of the wire support 2, semi-cylindrical wire sliding contact portions 4a, 4b and 4c, 4d protruded to each other are disposed, to both ends of the both side walls 4, 4, so that the circumferential surface of the round wire 6 is brought into point-to-point contact with that of the both side walls 4, 4 of the wire passage groove 3 when the correcting round wire 6 of a substantially circular cross section is inserted through the wire passage groove 3. Further, as shown in FIG. 4, which is a cross sectional view taken along lines II—II in FIG. 2, in the wire passage groove of the wire support 2, semi-cylindrical wire sliding contact portions 5a, 5b protruding upward are disposed at both longitudinal ends of the bottom surface 5 being in perpendicular to the longitudinal direction thereof respectively, so that the circumferential surface of the round wire 6 is brought into point-to-point contact with the circumferential surface 5 of the bottom surface 5 of wire passage groove 3 when the round wire 6 is inserted through the wire passage groove 3 (refer to FIG. 4).

On both longitudinal ends at the upper surface of the wire support 2, engaging grooves 9, 9 are disposed in parallel with the wire sliding contact portions 5a, 5b (perpendicular to the longitudinal direction). Each of the engaging grooves 9 is formed as a semi-cylindrical shape having substantially the same diameter as the binding wire 8. Further, downwarding hook-shaped engaging fingers 10a, 10b are disposed along the longitudinal direction on both sides of the wire support 2 except for both longitudinal ends. That is, the engaging fingers 10a, 10b situates between the engaging grooves 9, 9 disposed in parallel with each other to the upper surface of the wire support 2.

Figure 2:
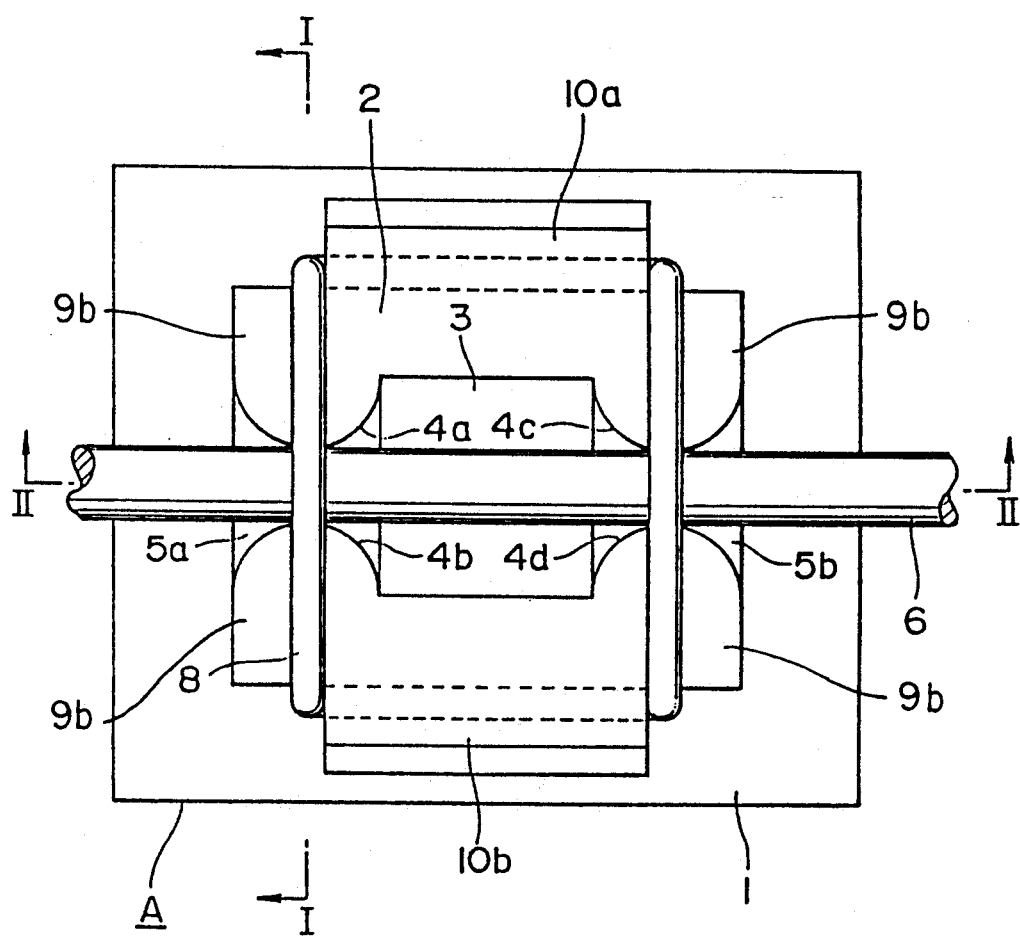
FIG. 2 is a front elevational view showing a state of winding a binding wire so as not to press a round wire.
Figure 3:
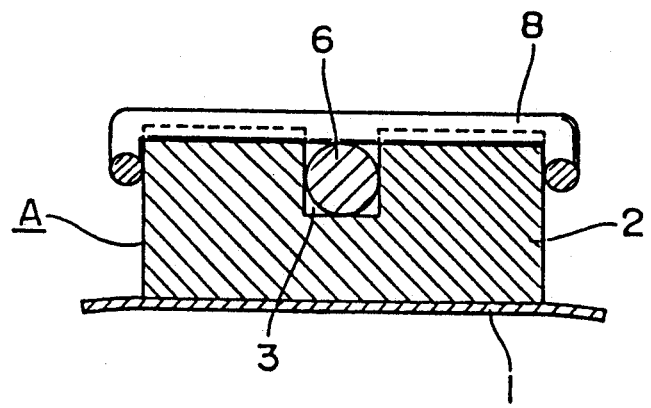
FIG. 3 is a cross sectional view taken along lines I—I in FIG. 2.

Accordingly, when the round wire 6 is extended under tension along the wire passage groove 3 of the individual bracket A, the binding wire 8 can be wound around the bracket A in a state along the engaging groove 9 and can be prevented from slipping-off by the engaging fingers 10a, 10b (refer to FIGS. 2 and 3). Then, since the round wire 6 is not pressed in this state by the binding wire 8, the wire passage grooves 3 of the bracket A bonded and fixed to the canine 19 can smoothly slide on the round wire 6 and, as a result, the period for the correction can be shortened by reducing the frictional force exerted between the wire passage groove 3 and the round wire 6.

Figure 5:
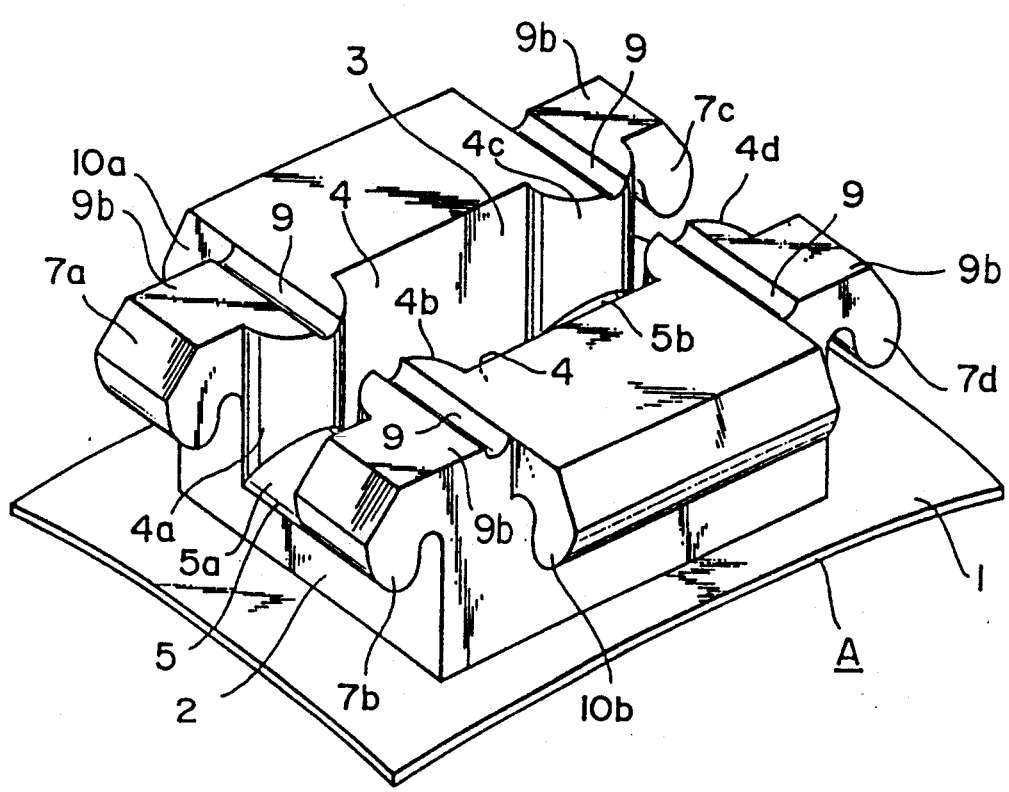
FIG. 5 is a perspective view illustrating another embodiment of a teeth straightening bracket according to the present invention.
Figure 6:
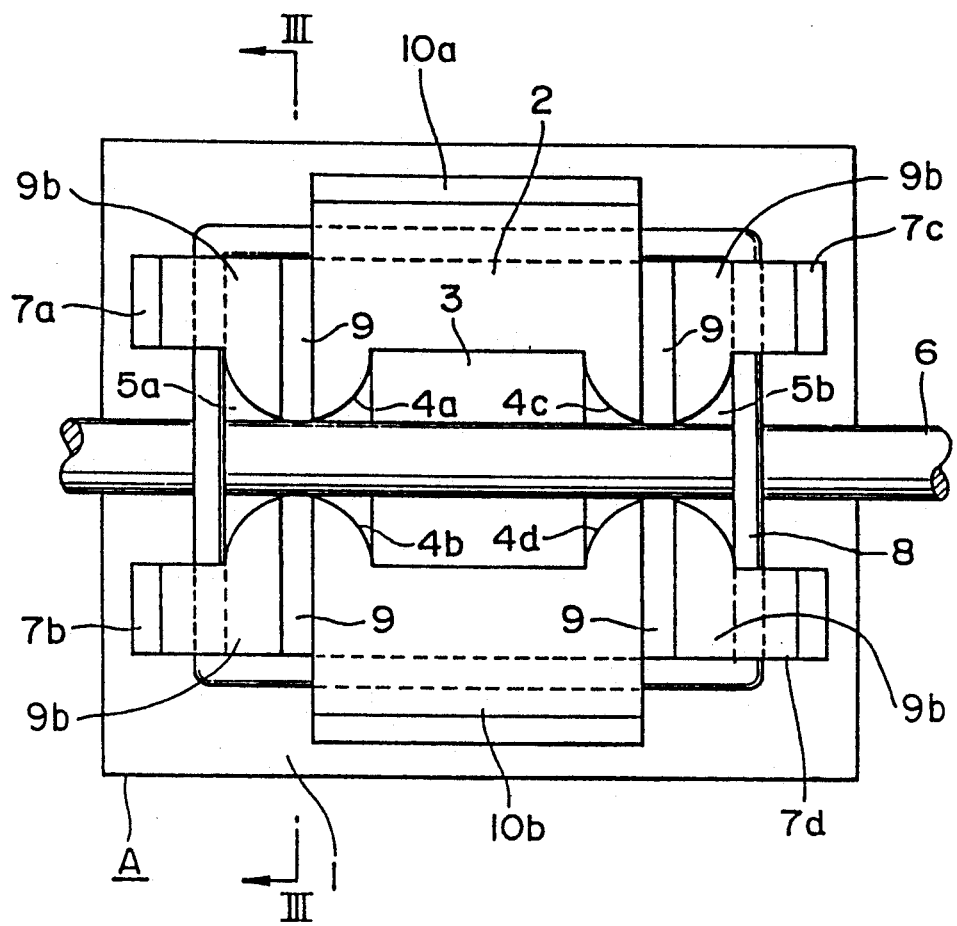
FIG. 6 is a front elevational view illustrating the state of winding a binding wire so as to press the round wire.
Figure 7:
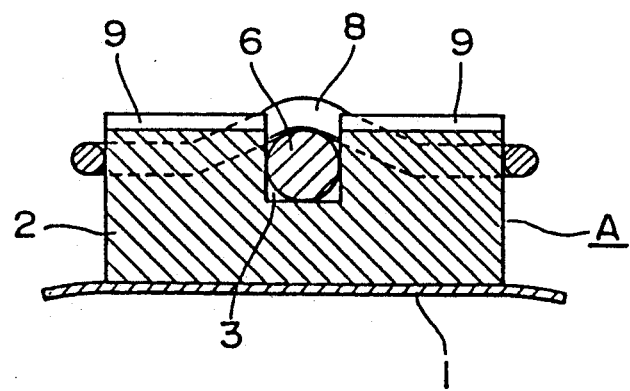
FIG. 7 is a cross sectional view taken along lines III—III in FIG. 6.

In another embodiment shown in FIGS. 5 to 7 (members in FIGS. 5 to 7 corresponding to the respective members in the embodiment shown in FIGS. 1 to 4 are shown by corresponding reference numerals), second engaging fingers 7a, 7b and 7c, 7d are disposed on both longitudinal ends of the wire support 2 being situated to the outside of the wire passage grooves 3 respectively.

In this modified embodiment, the binding wire 8 may be disposed along the engaging groove 9 in the same way as in the embodiment described previously or, if required, it may be passed below the second engaging fingers 7a–7d and then wound around the bracket A so as to press against the upper surface of the round wire 6 and prevented from slipping off by the second engaging fingers 7a, 7b and the 7c, 7d. Then, when it is bound in the latter way, since the bracket A bonded and fixed to each of teeth less slides on the round wire 6, this embodiment is more effective, for example, in a case of arranging the set of teeth in the forward and backward directions by the resiliency of the round wire 6 and then improving the twisting of a tooth.

In each of the above-mentioned embodiments, the engaging groove 9 is disposed to the upper surface of the wire support 2, and the binding wire 8 is passed through the engaging groove 9 upon winding the binding wire 8 around the bracket A so as not to press the round wire 6, but such an engaging groove 9 is not always necessary but the wire 8 may be extended along the upper surface of the wire support 2.

Figure 8:
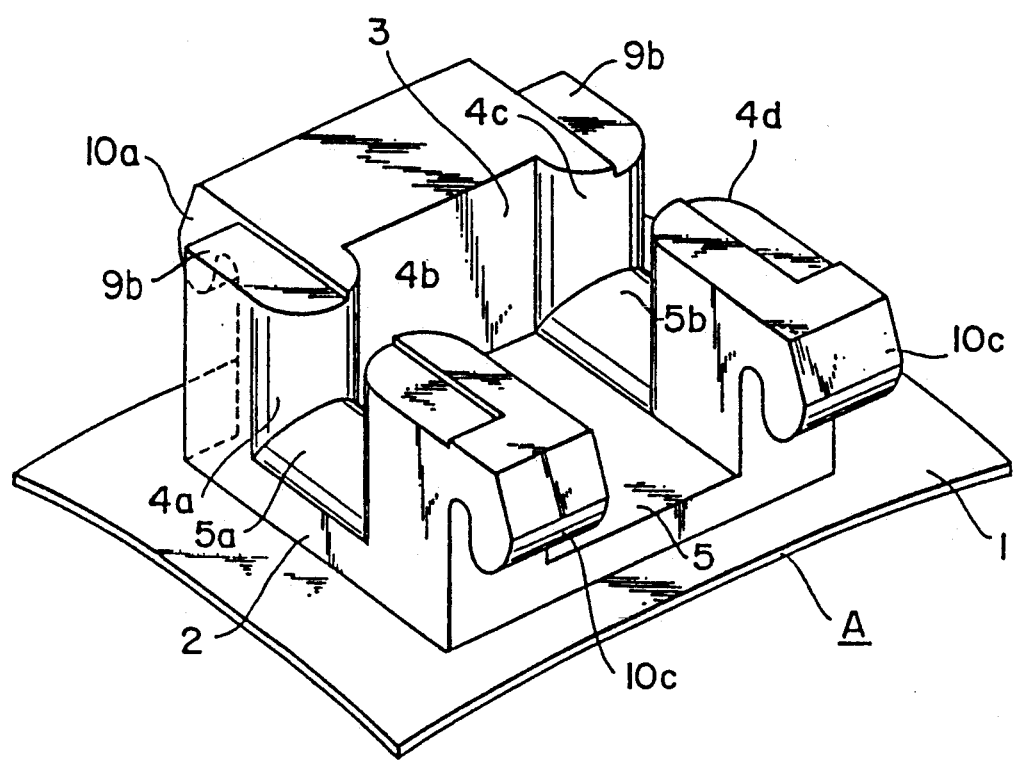
FIG. 8 is a perspective view illustrating a further embodiment of a teeth straightening bracket according to the present invention.
Figure 9:
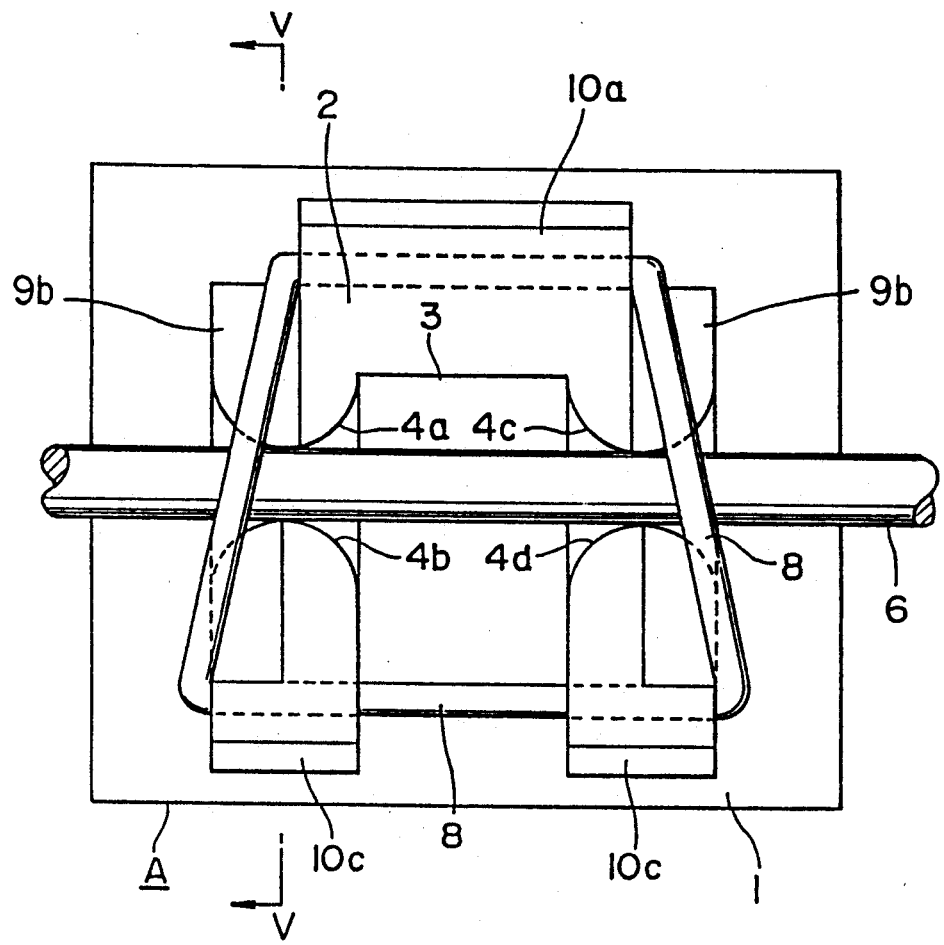
FIG. 9 is a front elevational view showing a state of winding a binding wire so as not to press the round wire.
Figure 10:
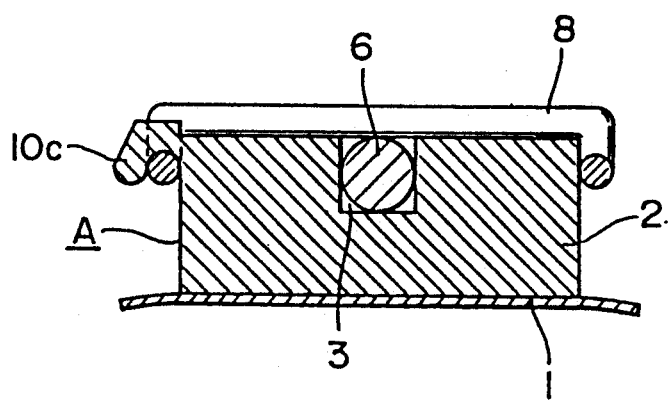
FIG. 10 is a cross sectional view taken along lines V—V in FIG. 9.
Figure 11:
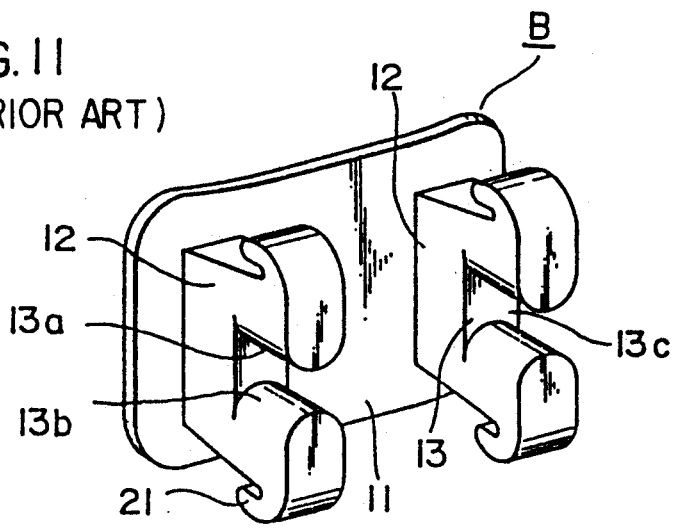
FIG. 11 is a perspective view illustrating an embodiment of the prior art.
Figure 12:
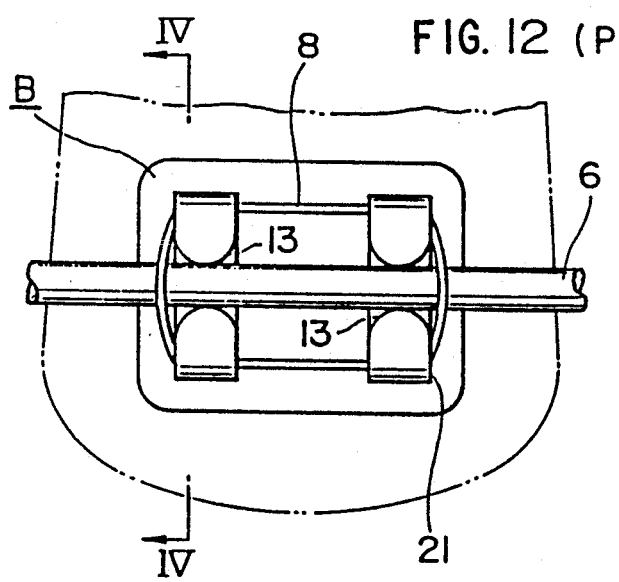
FIG. 12 is a front elevational view illustrating a state of winding a binding wire around the bracket in FIG. 11.
Figure 13:
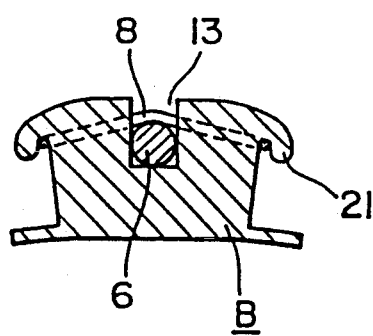
FIG. 13 is a cross sectional view taken along lines IV—IV in FIG. 12.
Figure 14:
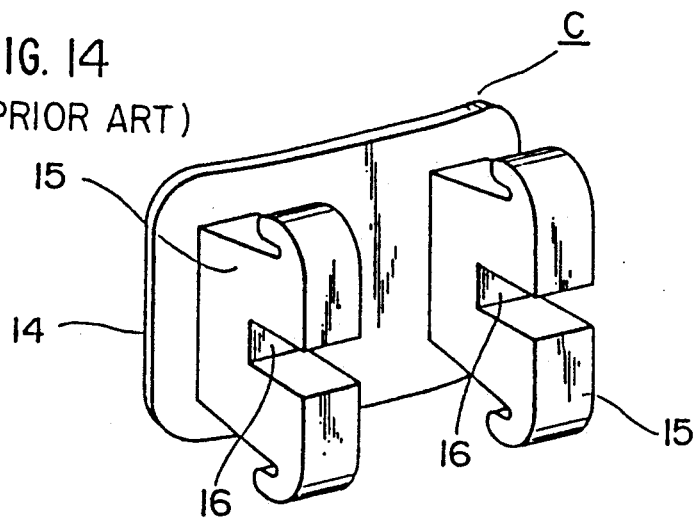
FIG. 14 is a perspective view illustrating another embodiment of the prior art.
Figure 15:
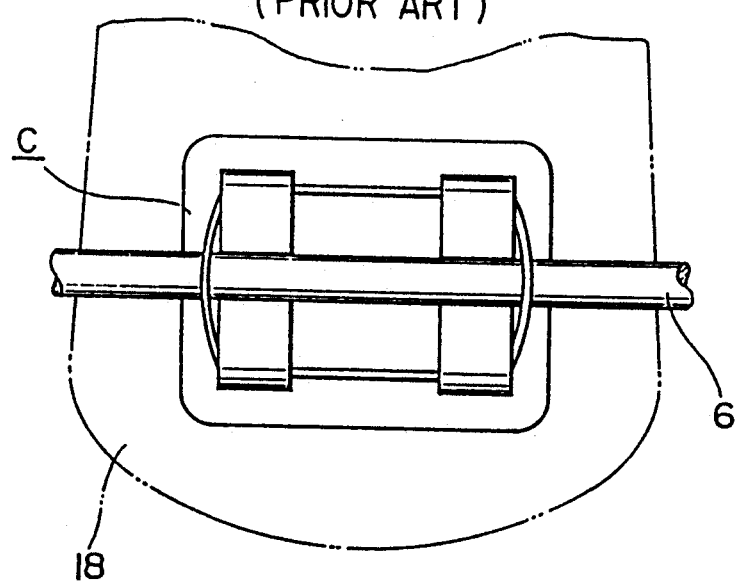
FIG. 15 is a front elevational view illustrating a state of bonding and fixing the bracket in FIG. 14 to the surface of a tooth and FIG. 16 is a schematic view illustrating the state of correction.
Figure 16:
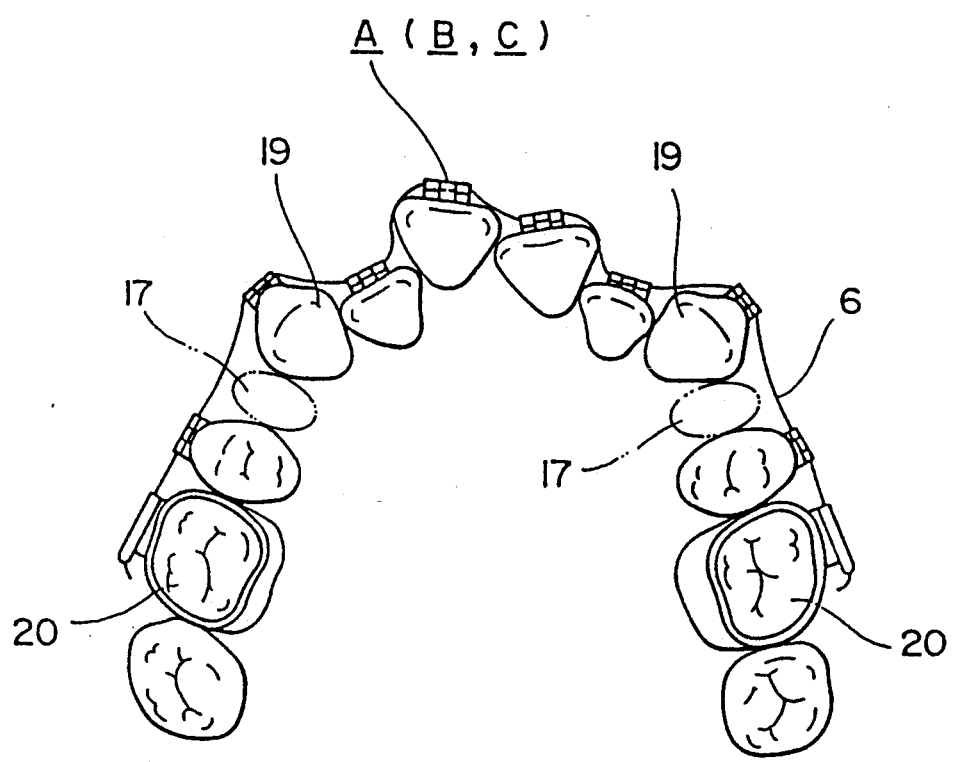
Figure 17:
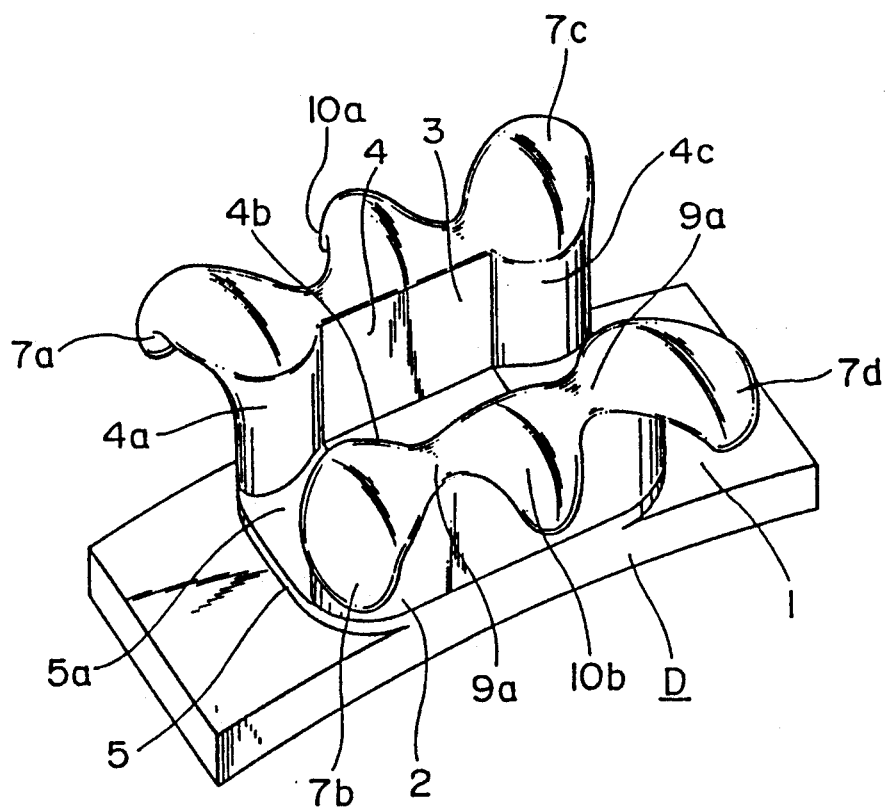
FIG. 17 is a perspective view illustrating a more practical embodiment according to the present invention.
Figure 18:
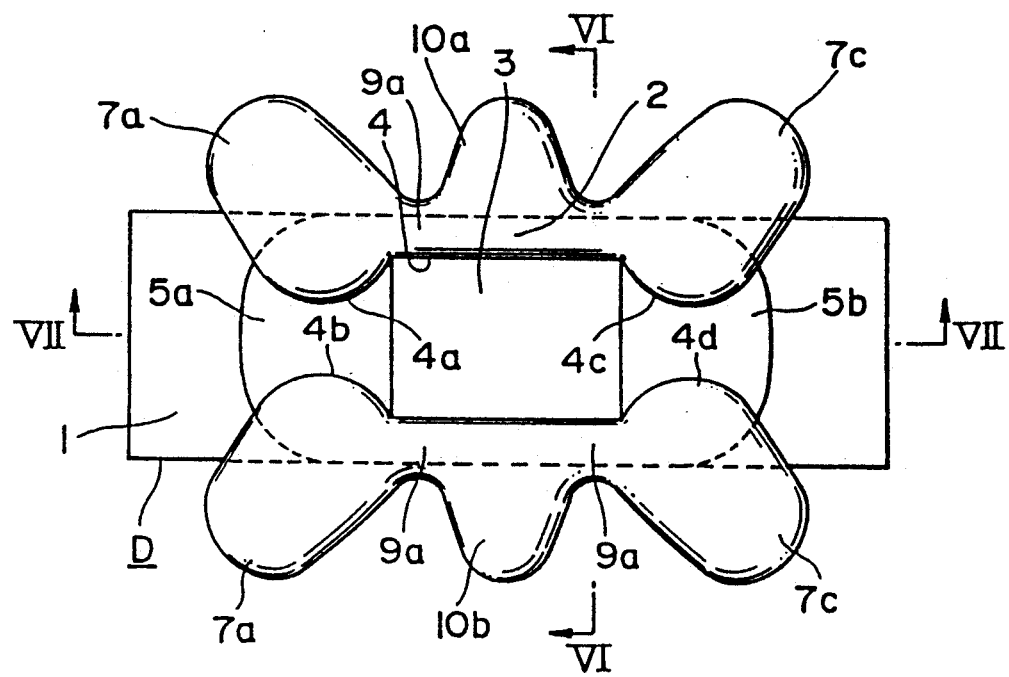
FIG. 18 is a plan view of the bracket in FIG. 17.
Figure 19:
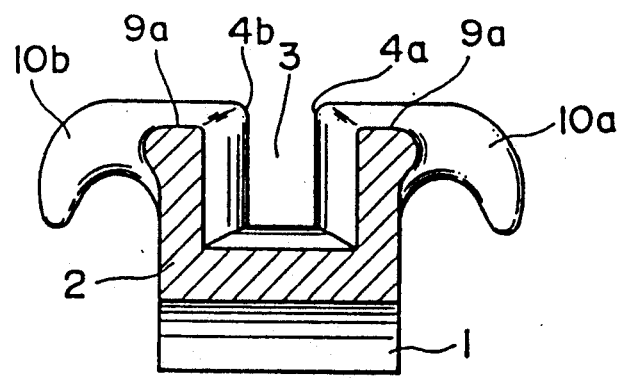
FIG. 19 is a cross sectional view taken along lines VI—VI in FIG. 18
Figure 20:
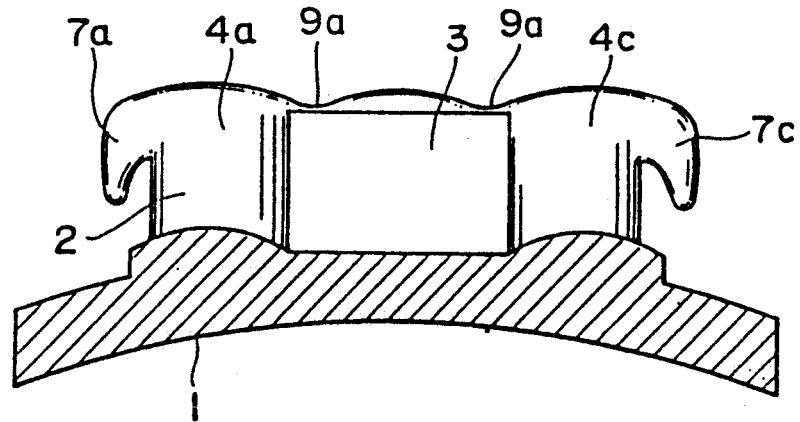
FIG. 20 is a cross sectional view taken along lines VII—VII in FIG. 18.

Further, although two engaging fingers 10a, 10b are disposed on both sides of the wire support 2 excepting for both longitudinal ends thereof, it is not always necessary for such a constitution, providing that the bonding wire rising from the engaging finger does not directly press the round wire. For instance, in FIGS. 8 to 10 showing a further embodiment of the present invention (members in FIGS. 8 to 10 corresponding to respective members in each of the embodiment described above are shown by corresponding reference numerals), the engaging finger 10a is disposed excepting for the both ends only on one side of the wire support 2, while the engaging finger 10c is disposed including the both ends thereof on the other side. Also in this case, when the round wire 6 is extended under tension in a state along the wire passage groove 3 of the individual bracket A, it is possible to wind the binding wire 8 around the bracket A in a state not to press the round wire 6 and along the upper surface of the wire support 2, and prevent it from slipping-off by the engaging fingers 10a, 10c (refer to FIGS. 9 and 10).

In a case of manufacturing and fabricating the tooth straightening bracket according to the present invention, it is preferred to make each of portions into a more smooth shape while considering actual feeling upon mounting, appearance or the like, and such a practical embodiment of the bracket is shown in FIGS. 17 to 20. In the figures, identical members with those in each of the embodiments described above are shown by identical reference numerals, excepting for indicating only the portion corresponding to the engaging groove 9 in each of the examples as a more smoothed engaging recess 9a.

INDUSTRIAL APPLICABILITY

The teeth straightening bracket according to the present invention is suitable to the effective correction for irregular set of teeth in various states in a short period of time.

I claim:
1. An orthodontic bracket comprising:
   a wire support;
   an archwire passage groove formed in said wire support to define a pair of side portions of said wire support standing apart and opposite each other, each side portion having an outer side wall and two ends;
   said archwire passage groove including a pair of protruding base portions perpendicular to its axis at both ends thereof, each one having an outwardly curved surface;
   two first engaging fingers for receiving a bonding wire thereunder and each having two free ends, said first engaging fingers provided to the outer side walls of each of said side portions of said wire support in such a manner that both ends of each of said side portions protrude beyond extension lines between opposing free ends of opposing first engaging fingers;
   an upper surface of each of said protruding ends having a width sufficient to permit a bonding wire to be passed thereon and a height sufficient to permit the bonding wire not to press an archwire down.
2. An orthodontic bracket according to claim 1, wherein each of said upper surfaces includes a bonding wire engaging groove forming a portion thereof and extending substantially perpendicular to said axis of said archwire passage groove.
3. An orthodontic bracket according to claim 1, wherein each of said protruding ends of each of said side portions further include a second engaging finger extending substantially parallel to said archwire passage groove for receiving a bonding wire thereunder.
4. An orthodontic bracket according to claim 3, wherein each of said upper surfaces includes a bonding wire engaging groove forming a portion thereof and extending substantially perpendicular to said axis of said archwire passage groove.
5. An orthodontic bracket according to claim 1, wherein one of said base portions and one of said upper surfaces of said protruding ends are each substantially aligned with a plane perpendicular to said axis of said archwire passage groove, wherein the other one of said base portions and the other one of said upper surfaces of said protruding ends are each substantially aligned with a plane perpendicular to said axis of said archwire passage groove, and wherein said height is defined from a top of said base portions to said upper surfaces of said protruding ends.
6. An orthodontic bracket according to claim 1, wherein said side portions comprise a single upstanding portion from which said first engaging fingers integrally extend.
7. An orthodontic bracket according to claim 1, wherein said first engaging fingers each comprise a single body portion integrally extending from said side portions.
8. An orthodontic bracket comprising:
   a wire support;
   an archwire passage groove formed in said wire support to define a pair of side portions of said wire support standing apart and opposite each other, each side portion having an outer side wall and two ends;
   said archwire passage groove including two pair of protruding wall portions perpendicular to its axis at both ends thereof, each one having an outwardly curved surface;
   two first engaging fingers for receiving a bonding wire thereunder and each having two free ends, said first engaging fingers provided to the outer side walls of each of said side portions of said wire support in such a manner that both ends of each of said side portions protrude beyond extension lines between opposing free ends of opposing first engaging fingers;
   an upper surface of each of said protruding ends having a width sufficient to permit a bonding wire to be passes thereon and a height sufficient to permit the bonding wire not to press an archwire down.
9. An orthodontic bracket according to claim 8, wherein each of said upper surfaces includes a bonding wire engaging groove forming a portion thereof and extending substantially perpendicular to said axis of said archwire passage groove.
10. An orthodontic bracket according to claim 8, wherein each of said protruding ends of each of said side portions further include a second engaging finger extending substantially parallel to said archwire passage groove for receiving a bonding wire thereunder.
11. An orthodontic bracket according to claim 10, wherein each of said upper surfaces includes a bonding wire engaging groove forming a portion thereof and extending substantially perpendicular to said axis of said archwire passage groove.
12. An orthodontic bracket according to claim 8, wherein one of said pairs of protruding wall portions and one of said upper surfaces of said protruding ends are each substantially aligned with a plane perpendicular to said axis of said archwire passage groove, wherein the other of said pairs of protruding wall portions and the other one of said upper surfaces of said protruding ends are each substantially aligned with a plane perpendicular to said axis of said archwire passage groove.
13. An orthodontic bracket according to claim 8, wherein said side portions comprise a single upstanding portion from which said first engaging fingers integrally extend.
14. An orthodontic bracket according to claim 8, wherein said first engaging fingers each comprise a single body portion integrally extending from said side portions.
15. An orthodontic bracket comprising:

a wire support;

an archwire passage groove formed in said wire support to define a pair of side portions of said wire support standing apart and opposite each other, each side portion having an outer side wall and two ends;

said archwire passage groove including a pair of protruding base portions and two pair of protruding wall portions perpendicular to its axis at both ends thereof, each one having an outwardly curved surface;

two engaging fingers for receiving a bonding wire thereunder and each having two free ends, said engaging fingers provided to the outer side walls of said side portions in such a manner that both ends of each of said side portions protrude beyond extension lines between opposing free ends of opposing engaging fingers;

an upper surface of each of said protruding ends having a width sufficient to permit a bonding wire to be passed thereon and a height sufficient to permit the bonding wire not to press an archwire down.

16. An orthodontic bracket according to claim 15, wherein each of said upper surfaces includes a bonding wire engaging groove forming a portion thereof and extending substantially perpendicular to said axis of said archwire passage groove.

17. An orthodontic bracket according to claim 15, wherein a center axis of each of said wall portions and a center axis of each of said base portions are aligned with said upper surface of said protruding ends perpendicular to said axis of said archwire passage groove, and wherein said height is defined from a top of said base portions to said upper surface of said protruding ends.

18. An orthodontic bracket according to claim 15, wherein said side portions comprise a single upstanding portion from which said first engaging fingers integrally extend.

19. An orthodontic bracket according to claim 15, wherein said first engaging fingers each comprise a single body portion integrally extending from said side portions.

20. An orthodontic bracket comprising:

a wire support;

an archwire passage groove formed in said wire support to define first and second side portions of said wire support standing apart and opposite each other, each side portion having an outer side wall and two ends;

said archwire passage groove including a pair of protruding base portions and two pair of protruding wall portions perpendicular to its axis at both ends thereof, each one having an outwardly curved surface;

a first engaging finger for receiving a bonding wire thereunder and having two free ends, said first engaging finger provided to said outer side wall of said first side portion in such a manner that said ends of said side portion protrude beyond said free ends of said first engaging finger;

each of said protruding ends having thereon a step which has a width sufficient to permit a bonding wire to be passed thereon and a height lower than the top plane thereof, but sufficiently high to permit the bonding wire not to press an archwire down;

two second engaging fingers for receiving the bonding wire thereunder provided to said outer side wall of said second side portion;

said second side portion having thereon steps having a width sufficient to allow a bonding wire to engage, and a height lower than the top plan thereof, but sufficiently high to permit the bonding wire not to press an archwire down.

21. An orthodontic bracket comprising:

a wire support;

an archwire passage groove formed in said wire support to define a pair of side portions of said wire support standing apart and opposite each other, each side portion having an outer side wall;

said archwire passage groove including a pair of protruding base portions and two pair of protruding wall portions perpendicular to its axis at both ends thereof, each one having an outwardly curved surface;

three engaging fingers for a bonding wire provided to the outer side wall of each of said side portions, respectively;

each of said outer side walls of each of said side portions including thereon bonding wire engaging recesses between said engaging fingers;

each of said bonding wire engaging recesses having a width sufficient to permit a bonding wire to be passed therethrough and a height sufficient to permit the bonding wire not to press an archwire down.

22. An orthodontic bracket comprising:

a wire support;

an archwire passage groove formed in said wire support to define a pair of side portions of said wire support standing apart and opposite each other, each side portion having an outer side wall and two upper surfaces mesio-distally displaced from each other;

two engaging fingers for receiving a bonding wire thereunder provided to the outer side walls of each of said side portions of said wire support; and a bonding wire engaging groove formed in each of said upper surfaces of said side portions substantially perpendicular to said axis of said archwire passage groove for receiving a bonding wire therein, said bonding wire engaging grooves having a height sufficient to permit the bonding wire not to press an archwire down.

* * * * *